United States Patent [19]

Holt et al.

[11] Patent Number: 4,937,237
[45] Date of Patent: Jun. 26, 1990

[54] PHOSPHINIC ACID SUBSTITUTED AROMATIC STEROIDS AS INHIBITORS OF STEROID 5-60 -REDUCTASE

[75] Inventors: Dennis A. Holt, Downingtown; Mark A. Levy, Wayne; Brian W. Metcalf, Radnor, all of Pa.

[73] Assignee: SmithKline Beckman Corporation, Philadelphia, Pa.

[21] Appl. No.: 290,057

[22] Filed: Dec. 23, 1988

[51] Int. Cl.$^5$ .................. A61K 31/66; A61K 31/675; A61K 31/665; C07J 1/00

[52] U.S. Cl. ...................................... 514/75; 514/79; 514/85; 514/86; 514/90; 514/91; 514/92; 514/100; 514/113; 514/125; 514/130; 540/23; 540/95; 540/100; 522/506; 522/626; 522/610; 522/611; 522/515

[58] Field of Search ................... 260/397, 397.3, 397.4, 260/397.45, 397.5; 540/23, 95, 100; 514/75, 79, 85, 86, 90, 91, 92, 100, 113, 125, 130

[56] References Cited

U.S. PATENT DOCUMENTS

| | | | |
|---|---|---|---|
| 4,179,453 | 12/1979 | Johnston | 260/397.1 |
| 4,191,759 | 3/1980 | Johnston et al. | 260/397.1 |
| 4,317,817 | 3/1982 | Blohm et al. | 260/397.4 |
| 4,361,578 | 11/1982 | Alig et al. | 568/372 |
| 4,377,584 | 3/1983 | Rasmusson et al. | 546/77 |

FOREIGN PATENT DOCUMENTS

| | | |
|---|---|---|
| 173516-A | 3/1986 | European Pat. Off. |
| 59-053417-A | 3/1984 | Japan |
| 60-116657-A | 6/1985 | Japan |
| 60-142941-A | 7/1985 | Japan |
| 60-146885-A | 8/1985 | Japan |

OTHER PUBLICATIONS

Petrakis et al., J. Am. Chem. Soc., 109, 2831-2833 (1987).
Imperato-McGinley, J. et al., J., Steroid Biochem, 11:637-645 (1979).
Hsia and Voight, J. Invest. Dermat., 62:224-227 (1973).
Robaire et al., J. Steroid Biochem. 8:307-310 (1977).
Blohm, T. R. et al., Biochem. Biophys. Res. Comm., 95:273-280 (1980).
Liang, T. et al., J. Steroid Biochem. 19, 385-390 (1983).
Petrow, V. et al., Steroids 38:121-140 (1981).
Dixon, M., Biochem. J., 55, 170 (1953).
Arth, J. Med. Chem. 6 617-618 (1963).
Neeman, J. Chem. Soc. Perkin I 2297 (1972).
Neeman, J. Chem. Soc. Perkin I 2300 (1972).
Hylarides, J. Org. Chem., 49, 2744 (1984).
Brooks et al., Steroids: 47:1-19 (Jan. 1986).

*Primary Examiner*—Joseph A. Lipovsky
*Attorney, Agent, or Firm*—Stuart R. Suter; Edward T. Lentz

[57] ABSTRACT

Invented are phosphinic acid substituted analogues of steroidal synthetic compounds, pharamaceutical compositions containing these compounds, and methods of using these compounds to inhibit steroid 5-α-reductase, including using these compounds to reduce or maintain prostate size.

22 Claims, No Drawings

PHOSPHINIC ACID SUBSTITUTED AROMATIC STEROIDS AS INHIBITORS OF STEROID 5-60 -REDUCTASE

FIELD OF THE INVENTION

The present invention relates to certain novel phosphinic acid substituted aromatic A ring analoques of steroidal synthetic compounds, pharmaceutical compositions containing these compounds and methods for using these compounds to inhibit mammalian steroid 5-α-reductase.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective production control results in excessive androgen hormone production. For example, acne vulgaris, seborrhea, female hirsutism, and benign prostatic hypertrophy are correlated with elevated androgen levels. Additionally, the incidence of male pattern baldness has been associated with high androgen levels.

Testosterone is the principal androgen secreted by the testes and is the primary androgenic steroid in the plasma of males. It now is known that 5-α-reduced androgens are the active hormones in some tissues such as the prostate and sebaceous gland. Circulating testosterone serves as a prohormone for dihydrotestosterone (DHT), its 5α-reduced analogue, in these tissues but not in others such as muscle and testis. Steroid 5-α-reductase is a NADPH-dependent enzyme that converts testosterone to DHT. The importance of this enzyme in male development was dramatically underscored by discovery of a genetic steroid 5-α-reductase deficiency in male psuedohermaphrodites. Imperato-McGinley, J., et al., (1979), *J. Steroid Biochem.* 11:637–648.

Recognition of the importance of elevated DHT levels in many disease states has stimulated many efforts to synthesize inhibitors of this enzyme. The structures of several known steroid 5-α-reductase inhibitors are shown in Table 1.

TABLE I

| | 5-α-Reductase Inhibitors | | |
|---|---|---|---|
| | | $K_i$ | Reference |
| (1) | COOH structure | $1.1 \times 10^{-6}$ M (Reversible) | Hsia and Voight 1973 |
| (2) | =O structure | $1 \times 10^{-6}$ M (Irreversible) | Robaire, et al., 1977 |
| (3) | OH structure | $3.5 \times 10^{-8}$ (Irreversible) | Blohm. et al., 1980 |
| (4) | amide structure | $5 \times 10^{-9}$ M (Reversible) | Liang, et at. 1983 |

| TABLE I-continued | | |
|---|---|---|
| 5-α-Reductase Inhibitors | | |
| | $K_i$ | Reference |
| (5) | $1.25 \times 10^{-6}$ M (Irreversible) | Petrow, et al., 1981 |

The first inhibitor described was the 17β-carboxylic acid (I) by Hsia and Voight in 1973. *J. Invest. Dermat.* 62:224–277. The secosteroid (2) was the next inhibitor to be described and also has found utility as an affinity label for 5-α-deductase. Robaire, B., et. al., (1977), *J. Steroid Biochem.* 8:307–310. The diazoketone (3) has been reported as a potent, time-dependent inhibitor of steroid 5-α-reductase. Blohm, T. R., et. al. (1980), *Biochem. Biophys. Res. Comm.* 95:273–280; U.S. Pat. No. 4,317,817, Mar. 2, 1982. Compound (4) is exemplary of a group of 4-aza steroid inhibitors of steroid 5-α-reductase described in U.S. Pat. No. 4,377,584 which issued Mar. 22, 1983, and in Liang, T., et al. (1983), *J. Steroid Biochem.* 19, 385–390. The 6-methylene steroid (5) also has been shown to be a time-dependent inactivator of steroid 5-α-reductase. Petrow, V., et. al. (1981), *Steroids* 38:121–140.

Other steroid 5-α-reductase inhibitors also have been described. U.S. Pat. No. 4,361,578 which issued June 2, 1986, describes a class of homosteroid enzyme inhibitors. U.S. Pat. No. 4,191,759 discloses amides of 17β-carboxy-4-androsten-3-one that are active as steroid 5-α-reductase inhibitors. Japanese Patents J60146855-A and J60116657-A disclose various aniline derivatives having numerous activities including 5-α-reductase inhibiting activity. Japanese Patent I60142941-A discloses phenyl-substituted ketones having 5-α-reductase inhibiting activity and European Patent EP173516-A discloses various phenyl-substituted amides having similar activity. Shiseido referenced terpene derivatives that are active inhibitors of steroid 5-α-reductase. Japanese Pat. No. J59053417-A.

Palladium-catalyzed substitutions of triflates, forming diethyl arylphosphonates, have been described in *J. Am. Chem. Soc.* 1987, 109, 2831–2833.

SUMMARY OF THE INVENTION

The present invention resides in the discovery that steroid 5-α-reductase is inhibited by certain phosphinic acid substituted aromatic A ring analogues of steroidal synthetic compounds. The compounds are potent enzyme inhibitors.

Presently preferred compounds of the invention, and compounds used in the preferred invented pharmaceutical compositions and the preferred invented methods include:

17β-(N,N-diisopropylcarboxamide)-estr-1,3,5(10)-triene-3-phosphinic acid,
17β-(N-tert-butylcarboxamide)-estr-1,3,5(10)-triene-3-phosphinic acid,
17β-(N,N-diisopropylcarboxamide)-estr-1,3,5(10),16-tetraene-3-phosphinic acid,
17β-(N-tert-butylcarboxamide)-estr-1,3,5(10),16-tetraene-3-phosphinic acid,
17β-(N,N-diisopropylcarboxamide)-estr-1,3,5(10),6,8-pentaene-3-phosphinic acid,
17β-(N,N-diisopropylcarboxamide)-2-methyl-estr-1,3,5(10)-triene-3-phosphinic acid,
17β-(N,N-diisopropylcarboxamide)-4-methyl-estr-1,3,5(10)-triene-3-phosphinic acid,
17β-(N,N-diisopropylcarboxamide)-estr-1,3,5(10),6-tetraene-3-phosphinic acid,
17β-(N,N-diisopropylcarboxamide)-2-chloro-estr-1,3,5(10)-triene-3-phosphinic acid, and
17β-(N,N-diisopropylcarboxamide)-4-chloro-estr-1,3,5(10)-triene-3-phosphinic acid.

In a further aspect of the invention there are provided processes useful in preparing the presently invented 5-α-reductase inhibiting compounds.

The invention also is a method for inhibiting 5-α-reductase activity in mammals, including humans, that comprises administering internally to a subject an effective amount of a presently invented 5-α-reductase inhibiting compound.

Included in the present invention are pharmaceutical compositions comprising a pharmaceutical carrier and compounds useful in the methods of the invention.

DETAILED DESCRIPTION OF THE INVENTION

The presently invented compounds that inhibit 5-β-reductase have the following Formula (I):

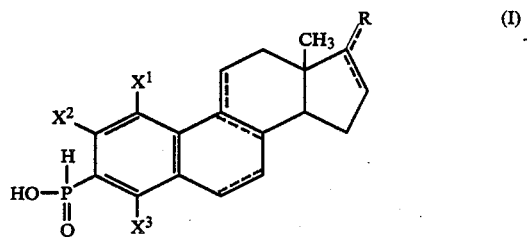

in which:
the B, C, and D rings have optional double bonds where indicated by the broken lines, provided that the C ring does not have a double bond when the B ring has a $C_8$–$C_9$ double bond, and provided that the D ring does not have a $C_{16}$–$C_{17}$ double bond when R represents two substituents or a divalent substituent;
$X^1$, $X^2$, and $X^3$ are any accessible combination of H, Cl, F, Br, I, $CF_3$, or $C_{1-6}$alkyl, OH, $C_{1-6}$alkoxy, CN, $NO_2$, $N(R^1)_2$, CHO, or $CO_2R^1$;
$R^1$ each independently is H or $C_{1-8}$alkyl; and
R is (1) α-hydrogen, α-hydroxyl, or α-acetoxy and/or
(a)

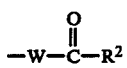

where W is a bond or $C_{1-12}$alkyl and $R^2$ is
(i) hydrogen,
(ii) hydroxyl,
(iii) $C_{1-8}$alkyl,
(iv) hydroxy $C_{1-8}$alkyl,
(v) $C_{1-18}$alkoxy,
(vi) $N(R^3)_2$, where each $R^3$ is independently selected from hydrogen, $C_{1-8}$alkyl, $C_{3-6}$cycloalkyl, phenyl; or both $R^3$ taken together with the nitrogen to which they are attached represent a 5–6 membered saturated ring comprising up to one other heteroatom selected from oxygen and nitrogen, or
(vii) $OR^4$, where $R^4$ is alkali metal or benzyl, or
(b) $-Alk-OR^5$, where Alk is $C_{1-12}$alkyl, and $R^5$ is
(i) phenyl $C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl, or
(vi) $C_{1-8}$alkyl, (2) $=CH-W-CO-R^2$ or $=CH-W-OR^5$, where W is a bond or $C_{1-12}$alkyl, and $R^2$ and $R^5$ have the same meaning as above and $R^5$ also is $C_{1-20}$alkylcarbonyl;

(3)

where the dashed bond replaces the 17-α-hydrogen
(4) α-hydrogen and β-NHCOR$^6$ where $R^6$ is $C_{1-12}$alkyl or β-$N(R^3)_2$ where $R^3$ has the same meaning as above,
(5) α-hydrogen and β-cyano,
(6) α-hydrogen and β-tetrazolyl, or
(7) keto;
or a pharmaceutically acceptable salt thereof.

As used herein, unless otherwise specified, $C_{1-n}$ alkyl and $C_{1-n}$ alk mean a straight or branched hydrocarbon chain having 1 to n carbons, Alk means a straight or branched hydrocarbon chain having 1 to 12 carbons, and "accessible combination" means any combination of substituents that is available by chemical synthesis and is stable.

Preferred among Formula (I) compounds are those in which $X^1$, $X^2$, and $X^3$ are H.

Also, preferred among the presently invented compounds are those having Formula (II):

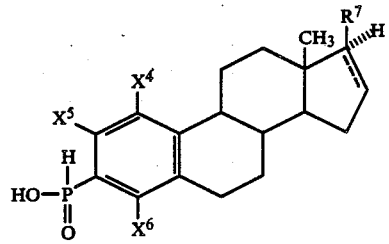

in which:
the D ring has an optional double bond where indicated by the broken line, provided that the 17α-hydrogen is not present when the $C_{16}$–$C_{17}$ double bond is present;
$X^4$, $X^5$ and $X^6$ are H;
$R^7$ is
(a) $CH(CH_3)CH_2OR^1$, or
(b) $CON(R^1)_2$, and
$R^1$ each independently is H or $C_{1-8}$alkyl;
or a pharmaceutically acceptable salt thereof.

Particularly preferred are Formula (II) compounds in which $R^7$ is N,N-diisopropylcarboxamide which is $-CON(C_3H_7)_2$.

Also preferred among the presently invented compounds are those having Formula (III):

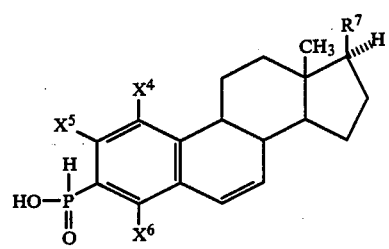

in which $R^7$, $R^1$, $X^4$, $X^5$ and $X^6$ are as defined for Formula (II). Additionally preferred among the presently invented compounds are those having Formula (IV):

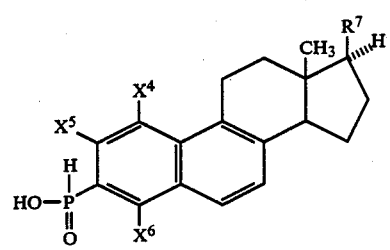

in which $R^7$, $R^1$, $X^4$, $X^5$ and $X^6$ are as defined for Formula (II).

Compounds of Formula (I) and their pharmaceutical salts are included in the pharmaceutical compositions of the invention and used in the methods of the invention.

As used above and throughout the remainder of the specification and claims, the carbons of the steroid nucleus are numbered and the rings are lettered in standard nomenclature as follows:

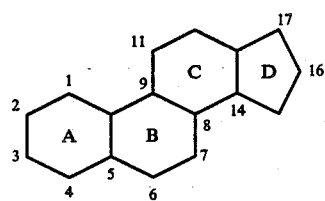

Schemes I and II show formation of Formula (Ia) compounds which are Formula (I) compounds in which R is replaced by $R^8$ which is R or moieties which can be converted to R by known chemical reactions such as described in J. Fried and J. Edwards, *Organic Reactions in Steroid Chemistry*, Pub: Van Nostrand Reinhold Company (1972). Reactions to convert $R^8$ to R may be performed on products of the synthetic pathway of Schemes I and II or, where appropriate or preferable, on certain intermediate in this synthetic pathway, as demonstrated in the following Examples.

preferably 0°, and reacted with a trihaloalkylsulfonic anhydride, preferably trifluoromethanesulfonic anhydride, to form compounds (b).

Compounds (b) then are mixed with a palladium compound, such as tetrakis(triphenylphosphine)palladium, a ligand for solubilizing the palladium catalyst, such as 1,3-bis(diphenylphosphino)propane, hypophosphorous acid crystals, an amine, such as triethylamine, and an organic solvent, such as dimethylformamide, and heated at 30° C. to 150° C., preferably 90° C., to yield phosphinic acid compounds (c).

Formula (Ia) compounds unsaturated at $C_{16}$-$C_{17}$ are prepared using modifications of the Scheme I procedure such as exemplified in Example 3 below.

SCHEME I

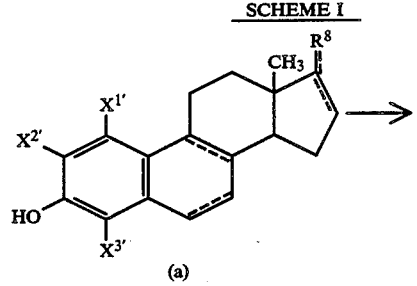

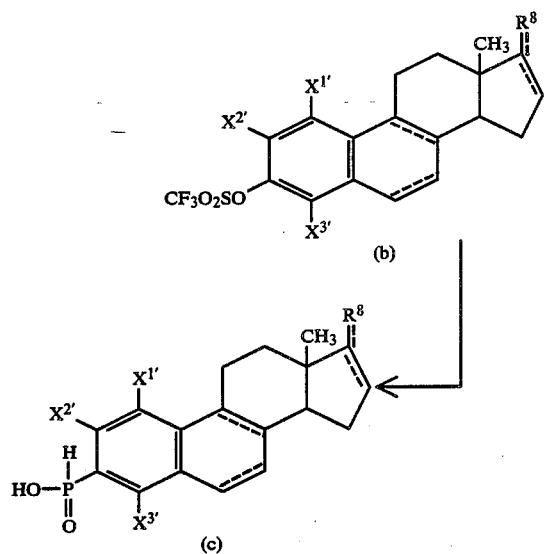

Scheme I depicts formation of Formula (Ia) compounds in which the broken lines indicate optional double bonds; and $X^{1'}$, $X^{2'}$, and $X^{3'}$, are $X^1$, $X^2$, and $X^3$ as in Formula (I) or moieties which can be converted to $X^1$, $X^2$, and $X^3$ by known procedures such as described in Carey and Sundberg, *Advanced Organic Chemistry* 2nd Ed. (1983), and exemplified in the examples below. The formula (a) starting materials are known and readily available or are synthesized from known precursors using known procedures. According to Scheme I, a compound (a) and a hindered aromatic base such as 2,6-lutidine in an appropriate organic solvent, preferably dichloromethane, is cooled to −20° C. to 20° C.,

SCHEME II

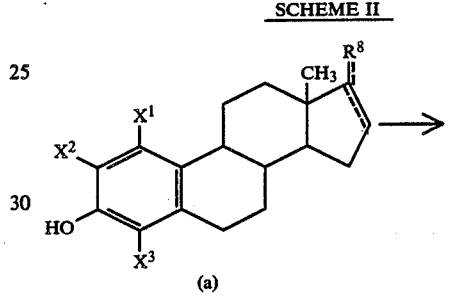

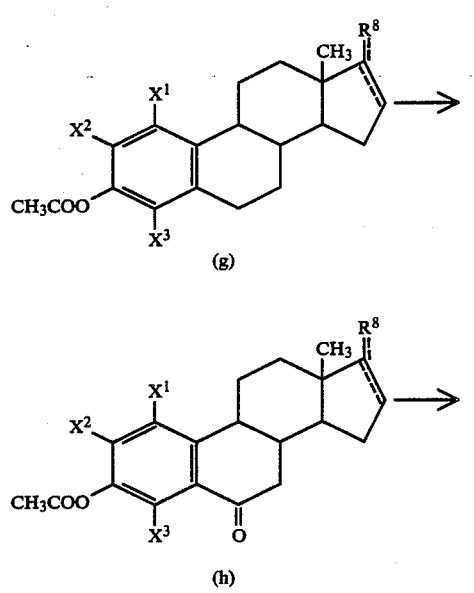

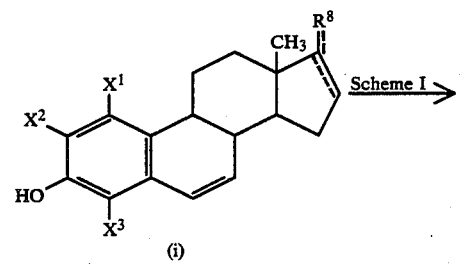

-continued
SCHEME II

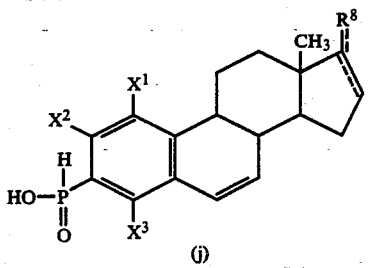

(j)

Scheme II outlines formation of Formula (Ia) compounds referred to above wherein the $C_6$–$C_7$ bond is unsaturated. The starting materials for Scheme II are compounds (a) from Scheme I. As outlined in Scheme II, compounds (a) in a suitable organic solvent, such as pyridine, are treated with a $C_{1-8}$alkyl anhydride, such as acetic anhydride, to yield formula (g) compounds. Compounds (g) then are treated with an oxidizing agent such as pyridinium chlorochromate, or preferably chromium trioxide ($CrO_3$), to form compounds (h).

Compounds (i) are prepared by treating compounds (h) with a reducing agent such as lithium aluminum hydride, diisobutylaluminum hydride, or preferably sodium borohydride ($NaBH_4$). Compounds (j), Formula (I) compounds in which the $C_6$–$C_7$ bond is unsaturated, then are prepared from compounds (i) as shown in Scheme I.

Formula (Ia) compounds, referred to above wherein the $C_9$–$C_{11}$ bond is unsaturated, are prepared using modifications of the Scheme I and II processes which will be readily apparent to those skilled in the art who are aware of these schemes. An example of such a modification is shown in Example 11.

Pharmaceutically acceptable acid addition salts of the compounds of the invention containing a basic group are formed where appropriate with strong or moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include nontoxic alkali metal and alkaline earth bases, for example, calcium, sodium, and potassium hydroxide; ammonium hydroxide, and nontoxic organic bases such as triethylamine, butylamine, piperazine, and (trihydroxymethyl)methylamine.

Because Formula (I) compounds inhibit steroid 5-α-reductase activity, they have therapeutic utility in treating diseases and conditions wherein decreases in DHT activity produce the desired therapeutic effect. Such diseases and conditions include acne vulgaris, seborrhea, female hirsutism, prostate diseases such as benign prostatic hypertrophy and prostatic carcinoma, and male pattern baldness.

A compound of the invention, 17β-(N,N-diisopropylcarboxamide)-estr-1,3,5(10)-triene-3-phosphinic acid, was tested for potency in inhibiting human steroid 5-α-reductase using tissue from hyperplastic human prostates. In determining potency in inhibiting the human enzyme, the following procedure was employed:

Frozen human prostates were thawed and minced into small pieces (5 mm$^3$). The tissue was homogenized in 3 to 5 volumes of 20 mM potassium phosphate buffer, pH 6.5, containing 0.33M sucrose, 1 mM dithiothreitol, and 50 μM NADPH with a Brinkmann Polytron (Sybron Corporation, Westbury, N.Y.). The solution was subjected to sonication for 3 to 5 minutes with a Sonifier (Branson Sonic Power Co.) followed by hand homogenization in a glass-to-glass Dounce homogenizer (Kontes Glass Company, Vineland, N.J.).

Prostatic particles were obtained by differential centrifugation at 600 or 1000×g for 20 minutes and 140,000×g for 60 minutes at 4° C. The pellet obtained from the 140,000×g centrifugation was washed with 5 to 10 tissue volumes of the buffer described above and recentrifuged at 140,000×g. The resulting pellet was suspended in 20 mM potassium phosphate buffer, pH 6.5, containing 20% glycerol, 1 mM dithiothreitol, and 50 μM NADPH. The suspended particulate solution was stored at −80° C.

A constant amount of [$^{14}$C]-testosterone (52 to 55 mCi/mmol, New England Nuclear, Boston, MA) in ethanol and varying amounts of the potential inhibitor in ethanol were deposited in test tubes and concentrated to dryness in a SAVANT Speed Vac. To each tube was added buffer, 20 μl of 10 mM NADPH and an aliquot of prostatic particulate solution to a final volume of 0.5 ml of 50 mM sodium citrate, pH 5.0. After incubating the solution at 37° C. for 20 to 30 minutes, the reaction was quenched by the addition of 4 ml ethyl acetate and 0.25 μmol each of testosterone, dihydrotestosterone, androstanediol, and androstanedione as carriers. The organic layer was removed to a second test tube and evaporated to dryness in vacuo. The residue was dissolved in 20 to 30 μl chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan, Inc., Washington, D.C.). The percent of recovered radiolabel converted to product was calculated, from which enzyme activity was determined. All incubations were conducted such that no more than 12% of the substrate (testosterone) was consumed.

The experimentally obtained data was computer fitted to a linear function by plotting the reciprocal of the enzyme activity (1/velocity) against the variable inhibitor concentration (Dixon, M. (1953), *Biochem. J.*, 55, 170). Assuming that the steroidal inhibitor is a competitive inhibitor against testosterone, a value for the inhibition constant ($K_i$) can be calculated from equation 1:

$$K_i = (B/A)/(S/K_m + 1) \qquad \text{Equation 1}$$

where B is the intercept on the 1/velocity axis, A is the slope of the line, S is the concentration of substrate (testosterone), and $K_m$ is the Michaelis-Menton constant of the substrate (testosterone) determined in a separate experiment to be 4.5 μM.

The value of $K_i$ for 17β-(N,N-diisopropylcarboxamide)-estr-1,3,5(10)-triene-3-phosphinic acid was determined to be 13 nM by the above testing procedure. The low value of $K_i$ determined demonstrates that this compound is a potent inhibitor of human steroid 5-α-reductase.

The compounds of Formula (I) are incorporated into convenient pharmaceutical dosage forms such as capsules, tablets, or injectable preparations. Solid or liquid pharmaceutically acceptable carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

The pharmaceutical preparations are made following conventional techniques of a pharmaceutical chemist involving steps such as mixing, granulating, and compressing, when necessary, for tablet forms, or mixing, filling and dissolving the ingredients, as appropriate, to give the desired oral or parenteral products.

Doses of the present compounds of Formula (I) in a pharmaceutical dosage unit as described above will be an efficacious, nontoxic quantity selected from the range of 0.001–100 mg/kg of active compound, preferably 0.01–10 mg/kg. The selected dose is administered to a human patient in need of steroid 5-α-reductase inhibition from 1–6 times daily, topically, orally, rectally, by injection, or continuously by infusion or less often than once a day depending on the pharmacokinetics of the compound. Oral dosage units for human administration preferably contain from 1 to 500 mg of active compound. Parenteral administration uses lower dosages. Oral administration is preferred and convenient for the patient.

The invented methods of inhibiting steroid 5-α-reductase activity in mammals, including humans, comprise administering internally to a subject an effective steroid 5-α-reductase inhibiting amount of a compound of Formula (I). The invented methods of reducing prostate size, which include methods of reducing the rate at which prostate size increases, comprise administering internally to a subject an effective amount of a Formula (I) compound.

The following examples illustrate preparation of Formula (I) compounds and pharmaceutical compositions containing these compounds. The examples are not intended to limit the scope of the invention as defined hereinabove and as claimed below.

EXAMPLE 1

17β-(N,N-Diisopropylcarboxamide)-estr-1,3,5(10)-triene-3-phosphinic Acid (i)
3-Methoxy-17-(trifluoromethylsulfonate)-estr-1,3,5(10),16-tetraene Methyl estrone (20 g, 50.4 mmol) and 2,6-di-tert-butyl-4-methylpyridine (15 g, 72 mmol) were dissolved in 500 ml $CH_2Cl_2$, and then treated with trifluoromethanesulfonic anhydride (15 g, 53 mmol) at room temperature for 6 hours. The mixture was then filtered, and the filtrate was washed with 5% HCl, saturated aqueous $NaHCO_3$, brine, and then dried and concentrated. The residue was chromatographed (silica, 5% ethyl acetate (EtOAc) in hexane) to yield the title compound (25.3 g, 95%).

(ii)
3-Methoxy-17-(N,N-diisopropylcarboxamide)-estr-1,3,5(10),16-tetraene

A mixture of 3-methoxy-17-(trifluoromethylsulfonate)-estr-1,3,5(10),16-tetraene (25 g, 47 mmol), bis(triphenylphosphine)palladium (II) acetate (3 g), triethylamine (18 ml), diisopropylamine (100 ml), and dimethylformamide (200 ml) was heated at 60° C. under an atmosphere of carbon monoxide for 12 hours. The mixture was then concentrated, diluted with 500 ml $H_2O$ and thoroughly extracted with $CHCl_3$. The organic extract was washed with 5% HCl, saturated aqueous $NaHCO_3$, brine and then concentrated to a thick oil. Chromatography (silica, 10% EtOAc in hexane) yielded the title compound as a white solid (16 g).

(iii)
3-Methoxy-estr-1,3,5(10)-triene-17β-(N,N-diisopropylcarboxamide)

3-Methoxy-17-(N,N-diisopropylcarboxamide)-estr-1,3,5(10),-16-tetraene (16 g) dissolved in 500 ml 3:1 EtOAc-EtOH was hydrogenated over $PtO_2$ (5 g) at 1 atm. overnight.

The mixture was filtered and concentrated to yield the title compound (14.25 g).

(iv)
Estr-1,3,5(10)-triene-3-ol-17β-(N,N-diisopropylcarboxamide)

To a 0° C. solution of 3-methoxy-estr-1,3,5(10)-triene-17β-(N,N-diisopropylcarboxamide) (4.8 g, 12 mmol) in dichloromethane (150 ml) was added a dichloromethane solution of boron tribromide (45 ml, 1M, 45 mmol). The resulting solution was stirred at 0° C., for 2 hours and then at 25° C. for 30 minutes. After cooling back to 0° C., methanol (50 ml) was added carefully and the volatiles were then removed in vacuo. The residue was redissolved in dichloromethane and washed with water, dried, treated with silica gel and charcoal, filtered and concentrated. Trituration of the residue with acetone afforded 4.7 g (98%) of estr-1,3,5(10)-triene-3-ol-17β-(N,N diisopropylcarboxamide) as a white solid.

(v)
3-(Trifluoromethylsulfonate)-estr-1,3,5(10)-triene-17β-(N,N-diisopropylcarboxamide)

A solution of estr-1,3,5(10)-triene-3-ol-17β-(N,N-diisopropylcarboxamide) (11.15 g, 29.1 mmol) and 2,6-lutidine (5.1 ml, 45 mmol) in 300 ml dichloromethane at 0° C. was treated with trifluoromethanesulfonic anhydride (5.9 ml, 36 mmol). After 1 hour the mixture was filtered, concentrated, and chromatographed (silica, 20% EtOAc in hexane) to yield the title compound (9.1 g).

(vi)
17β-(N,N-Diisopropylcarboxamide)-estr-1,3,5(10)-triene-3-phosphinic Acid

A mixture of 3-(trifluoromethylsulfonate)-estr-1,3,5(10)-triene-17β-(N,N-diisopropylcarboxamide)

(150 mg. 0.285 mmole), triethylamine (84 μL, 0.63 mmole), dimethylformamide (3 mL), tetrakis (triphenylphosphine) palladium (0) (13 mg, 0.009 mmole), 1,3-bis (diphenylphosphino) propane (3.7 mg, 0.009 mmole) and hypophosphorous acid crystals (42 mg) was heated under an argon atmosphere in an oil bath held at 90° C. for 6 hours. The reaction was quenched with ice, extracted with dichloromethane and the combined organic layer was washed with dilute HCl, water, 5% NaHCO$_3$ solution and brine. The dried, concentrated product was a dark oil which was chromatographed on a C$_{18}$-reverse phase flash column with a 70/30 MeOH-phosphate buffer (20 mmole, pH 6.6). The fractions were evaporated and acidified to pH 3 to afford a beige precipitate, which was triturated with acetonitrile to give the title compound; m.p. 230°-234° C. Proton NMR showed a doublet for P-H at 6.4 and 8.6 ppm.

EXAMPLE 2

17β-(N-tert-Butylcarboxamide)-estr-1,3,5(10)-triene-3-phosphinic Acid

The title compound is prepared according to Example 1 by substituting tert-butylamine for diisopropylamine in step (ii).

EXAMPLE 3

17β-(N,N-Diisopropylcarboxamide)-estr-1,3,5(10),16-tetraene-3-phosphinic Acid

The title compound is prepared according to Example 1 (vi) by substituting 3-(trifluoromethylsulfonate)-estr-1,3,5(10),16-tetraene-17β-(N,N-diisopropylcarboxamide) for 3-(trifluoromethylsulfonate)-estr-1,3,5(10)-triene-17β-(N,N-diisopropylcarboxamide).

EXAMPLE 4

17β-(N-tert-Butylcarboxamide)-estr-1,3,5(10),16-tetraene-3-phosphinic Acid

The title compound is prepared according to Example 1 (vi) by substituting 3-(trifluoromethylsulfonate)-estr-1,3,5(10),16-tetraene-17β-(N-tert-butylcarboxamide) for 3-(trifluoromethylsulfonate)-estr-1,3,5(10)-triene-17β-(N,N-diisopropylcarboxamide).

EXAMPLE 5

17β-(N,N-Diisopropylcarboxamide)-estr-1,3,5(10),6,8-pentaene-3-phosphinic Acid

The title compound is prepared according to Example 1 by substituting 1,3,5(10),6,8-estrapentaene-3-methoxy-17-one for methyl estrone.

EXAMPLE 6

17β-(N,N-Diisopropylcarboxamide)-2-methyl-estr-1,3,5(10)-triene-3-phosphinic Acid The title compound is prepared according to Example 1 by substituting methyl 2-methyl-estrone for methyl estrone.

EXAMPLE 7

17β-(N,N-Diisopropylcarboxamide)-4-methyl-estr-1,3,5(10)-triene-3-phosphinic Acid The title compound is prepared according to Example 1 by substituting methyl 4-methyl-estrone for methyl estrone.

EXAMPLE 8

17β-(N,N-Diisopropylcarboxamide)-estr-1,3,5(10),6-tetraene-3-phosphinic Acid (i)

3-Methoxy-17-(trifluoromethylsulfonate)-estr-1,3,5(10),16-tetraene

Methyl estrone (60 mmol) and 2,6-di-tert-butyl-4-methylpyridine (27 g, 130 mmol) are dissolved in 500 ml of dichloromethane and the solution is cooled to 0° C. Trifluoromethanesulfonic anhydride (45.3 g, 160 mmol) is then slowly added to the solution. The resulting solution is stirred at 0° C. for 2 hours and then at 25° C. for 4 hours. The solution is then washed with 10% aqueous HCl, saturated aqueous NaHCO$_3$, brine, and then dried and concentrated. Chromatography (silica gel, 5% EtOAc in hexane) affords 3-methoxy-17-(trifluoromethylsulfonate)-estr0 1,3,5(10),16-tetraene.

(ii)

3-Methoxy-17-(N,N-diisopropylcarboxamide)-estr-1,3,5,(10),16-tetraene

A mixture of 3-methoxy-17-(trifluoromethylsulfonate)-estr-1,3,5(10),16-tetraene (26 mmol), palladium (II) acetate (500 mg), triphenylphosphine (1.1 g), triethylamine (9 ml), diisopropylamine (50 ml), and dimethylformamide (100 ml) are heated at 60° C. under an atmosphere of carbon monoxide for 5 hours. The mixture is concentrated, diluted with water, and thoroughly washed with dichloromethane. The combined organic extracts are then washed with 10% aqueous HCl, saturated aqueous NaHCO$_3$, dried, and concentrated to a dark oil. Chromatography of the oil on silica gel (15% EtOAc in hexane) affords 3-methoxy-17-(N,N-diisopropylcarboxamide)-estr-1,3,5(10),16-tetraene.

(iii)

3-Methoxy-17β-(N,N-diisopropylcarboxamide)-estr-1,3,5(10)-triene

3-Methoxy-17-(N,N-diisopropylcarboxamide)-estr-1,3,5(10),16-tetraene (17.5 mmol) dissolved in 125 ml EtOAc and 45 ml ethanol is hydrogenated over platinum oxide (800 mg) at 1 atm. for 3 hours. The catalyst is removed by filtration and the filtrate concentrated to yield 3-methoxy-17β-(N,N-diisopropylcarboxamide)-estr-1,3,5(10)-triene.

(iv)

Estr-1,3,5(10)-triene-3-ol-17β-(N,N-diisopropylcarboxamide)

To a 0° C. solution of 3-methoxy-17β-(N,N-diisopropylcarboxamide)-estr-1,3,5(10)-triene (4.8 g, 12 mmol) in dichloromethane (150 ml) is added a dichloromethane solution of boron tribromide (45 ml, 1M, 45 mmol). The resulting solution is stirred at 0° C., for 2 hours and then at 25° C. for 30 minutes. After cooling back to 0° C., methanol (50 ml) is added carefully and the volatiles were then removed in vacuo. The residue is redissolved in dichloromethane and washed with water, dried, treated with silica gel and charcoal, filtered and concentrated. Trituration of the residue with acetone affords 4.7 g (98%) of estr-1,3,5(10)-triene-3-ol-17β-(N,N-diisopropylcarboxamide) as a white solid.

(v)
Estr-1,3,5(10)-triene-3-acetoxy-17β-(N,N-diisopropylcarboxamide)

A solution of estr-1,3,5(10)-triene-3-ol-17β-(N,N-diisopropylcarboxamide) (4.7 g, 12.3 mmol) in 100 ml pyridine is treated with 70 ml acetic anhydride for 18 hours. The reaction mixture is poured into ice water and extracted with ethyl acetate. The organic extract is washed with 10% aqueous HCl, water, brine, and concentrated to afford 5.2 g (100%) of estr-1,3,5(10)-triene-3-acetoxy-17β-(N,N-diisopropylcarboxamide).

(vi)
6-Oxo-estr-1,3,5(10)-triene-3-acetoxy-17β-(N,N-diisopropylcarboxamide)

To a solution of estr-1,3,5(10)-triene-3-acetoxy-17β-(N,N-diisopropylcarboxamide) (5 g, 12 mmol) in 17 ml glacial acetic acid is added a solution of chromium trioxide (3.5 g) in 23 ml acetic acid and 4 ml water. After stirring for 18 hours, ethanol 20 ml) is added and the resulting mixture is extracted with ethyl ether. The ethereal extract is washed with water, saturated aqueous NaHCO$_3$, dried over sodium sulfate, and concentrated. Chromatography (silica el, 25% EtOAc in hexane) affords 400 mg (8%) of 6-oxo-estr-1,3,5(10)-triene-3-acetoxy-17β-(N,N-diisopropylcarboxamide), m.p. 223°-224° C. (recrystallized from methanol).

(vii)
Estr-1,3,5(10),6-tetraene-3-ol-17β-(N,N-diisopropylcarboxamide)

A suspension of 6-oxo-estr-1,3,5(10)-triene-3-acetoxy-17β-(N,N-diisopropylcarboxamide) (400 mg, 0.9 mmol) in 40 ml methanol at 15° C. is treated with 800 mg of NaBH$_4$ for 1 hour. HCl (3.5 ml) and water (3.5 ml) is added and the resulting mixture is cooled, diluted with water and extracted with ethyl acetate. The organic extract is washed with water and brine, and dried and concentrated to a solid. Chromatography (silica gel, 5% EtOAc in methylene chloride) affords 200 mg (58%) of estr-1,3,5(10),6-tetraene-3-ol-17β-(N,N-diisopropylcarboxamide), m.p. 276°-279° C.

(viii)
17β-(N,N-Diisopropylcarboxamide)-3-(trifluoromethylsulfonate)-estr-1,3,5(10),6-tetraene The title compound is prepared according to Example 1 (v) by substituting estr-1,3,5(10),6-tetraene-3-ol-17β-(N,N-diisopropylcarboxamide) for estr-1,3,5(10) triene-3-ol-17β-(N,N-diisopropylcarboxamide).

(ix)
17β-(N,N-Diisopropylcarboxamide)-estr-1,3,5(10),6-tetraene 3-phosphinic Acid The title compound is prepared according to Example 1 (vi) by substituting 17β-(N,N-diisopropylcarboxamide)-3-(trifluoromethylsulfonate)-estr-1,3,5(10),6-tetraene for 3-(trifluoromethylsulfonate)-estr-1,3,5(10)-triene-17β-(N,N-diisopropylcarboxamide) in Example 1 (vi).

EXAMPLE 9
Estr-1,3,5(10)-triene-17-one-3-phosphinic Acid (i)
3-(Trifluoromethylsulfonate)-estr-1,3,5(10)-triene-17-one Estrone is dissolved in dichloromethane, cooled to 0°, and treated with 2,6-lutidine and trifluoromethanesulfonic anhydride for two hours. Aqueous workup yields 3-(trifluoromethylsulfonate)-estr-1,3,5(10)-triene-17-one.

(ii) Estr-1,3,5(10)-triene-17-one-3-phosphinic Acid

The title compound is prepared according to Example 1 (vi) by substituting 3-(trifluoromethylsulfonate)-estr-1,3,5(10)-triene-17-one in Example 1 (vi) for 3-(trifluoromethylsulfonate)-estr-1,3,5(10)-triene-17β-(N,N-diisopropylcarboxamide).

EXAMPLE 10
2',3'-Tetrahydrofuran-2'-spiro-17-(1,3,5(10)-estratriene-3-phosphinic Acid)

The title compound is prepared according to Example 1 (iv through vi) by substituting 2',3'α-tetrahydrofuran-2'-spiro-17-(3-methoxy-1,3,5-estratriene), prepared according to Arth (*J. Med. Chem.* 6 617–618 (1963)), for 3-methoxy-estr-1,3,5(10)-triene-17β-(N,N-diisopropylcarboxamide).

EXAMPLE 11
17β-(N,N-Diisopropylcarboxamide)-estr-1,3,5(10),9(11)-tetraene-3-phosphinic Acid (i)
Estr-1,3,5(10),9(11)-tetraene-3-ol-17β-(N,N-diisopropylcarboxyamide)

A solution of estr-1,3,5(10)-triene-3-ol-17β-(N,N-diisopropylcarboxamide) (380 mg, 1 mmol) in 10 ml dioxane is treated with 2,3-dichloro-5,6-dicyano-1,4-benzoquinone (250 mg, 1.1 mmol) for two hours. The reaction mixture is diluted with ethyl acetate, washed with saturated aqueous NaHCO$_3$, dried, and concentrated Chromatography of the residue yields estr-1,3,5(10),9(11)-tetraene-3-ol-17β-(N,N-diisopropylcarboxamide).

(ii)
17β-(N,N-Diisopropylcarboxamide)-estr-1,3,5(10),-9(11)-tetraene-3-phosphinic Acid The title compound is prepared according to Example 1 (v and vi) by substituting estr-1,3,5(10),9(11)-tetraene-3-ol-17β-(N,N-diisopropylcarboxamide) in Example 1 (v) for estr-1,3,5(10)-triene-3-ol-17β-(N,N-diisopropylcarboxamide) and subsequently proceeding with the step (vi) of Example 1.

EXAMPLE 12
17β-(N,N-Diisopropylcarboxamide)-2-bromo-estr-1,3,5(10)-triene-3-phosphinic Acid and 17β-(N,N-Diisopropylcarboxamide)-4-bromo-estr-1,3,5(10)-triene-3-phosphinic Acid (i)
2-Bromo-estr-1,3,5(10)-triene-3-ol-17β-(N,N-diisopropylcarboxamide) and
4-Bromo-estr-1,3,5(10)-triene-3-ol-17β-(N,N-diisopropylcarboxamide)

A solution of estr-1,3,5(10)-triene-3-ol-17β-(N,N-diisopropylcarboxamide) (1.85 g, 4.82 mmol) in 185 ml of warm acetic acid is cooled to 20° C. and 4.48 ml (4.82 mmol) of a 1.08M solution of bromine in acetic acid is added slowly. After stirring at ambient temperature for 5 min., the reaction mixture is poured into ice water and extracted twice with dichloromethane. The combined dichloromethane extracts are washed twice with water, dried over anhydrous MgSO4 and concentrated. Chromatography (silica gel, 2% followed by 5% ether in dichloromethane) affords 0.39 g of 2-bromo-estr-1,3,5(10)-triene-3-ol-17β-(N,N-diisopropylcarboxamide) and 0.75 g of 4-bromo-estr-1,3,5(10)-triene 3-ol-17β-(N,N-diisopropylcarboxamide).

(ii)

17β-(N,N-Diisopropylcarboxamide)-2-bromo-3-(trifluoromethylsulfonate)-estr-1,3,5(10)-triene and
17β-(N,N-Diisopropylcarboxamide)-4-bromo-3-(trifluoromethylsulfonate)-estr-1,3,5(10)-triene A solution of 2-bromo-estr-1,3,5(10)-triene-3-ol-17β-(N,N-diisopropylcarboxamide) (0.393 g, 0.850 mmol) in dichloromethane (20 ml) is cooled with an ice bath and treated successively with lutidine (0.149 ml, 1.275 mmol), 4-dimethylaminopyridine (20.8 mg, 0.17 mmol) and trifluoromethanesulfonic anhydride (0.214 ml, 1.275 mmol). The reaction mixture is stirred at room temperature for two hours and then concentrated at ambient temperature. The residue is treated with ether and 10% HCl, then the organic layer is washed with water followed by 5% NaHCO3, dried and concentrated to yield 0.481 g (95%) of 17β-(N,N-diisopropylcarboxamide)-2-bromo-3-(trifluoromethylsulfonate)-estr-1,3,5(10)-triene.

Substitution of 4-bromo-estr-1,3,5(10)-triene-3-ol-17β-(N,N-diisopropylcarboxamide) for 2-bromo-estr-1,3,5(10)-triene-3-ol-17β-(N,N-diisopropylcarboxamide) affords 17β-(N,N-diisopropylcarboxamide)-4-bromo-3-(trifluoromethylsulfonate)-estr-1,3,5(10)-triene.

(iii)

17β-(N,N-Diisopropylcarboxamide)-2-bromo-estr-1,3,5(10)-triene-3-phosphinic Acid and
17β-(N,N-Diisopropylcarboxamide)-4-bromo-estr-1,3,5(10)-triene-3-phosphinic Acid Substitution of 17β-(N,N-diisopropylcarboxamide)-2-bromo-3-(trifluoromethylosulfonate)-estr-1,3,5(10)-triene for 3-(trifluoromethylsulfonate)-estr-1,3,5(10)-triene-17β-(N,N-diisopropylcarboxamide) as in Example 1 (vi) yields 17β-(N,N-diisopropylcarboxamide)-2-bromo-estr-1,3,5(10)-triene-3-phosphinic acid.

Substitution of 17β-(N,N-diisopropylcarboxamide)-4-bromo-3-(trifluoromethylsulfonate)-estr-1,3,5(10)-triene for 3-(trifluoromethylsulfonate)-estr-1,3,5(10)-triene-17β-(N,N-diisopropylcarboxamide) as in Example 1 (vi) yields 17β-(N,N-diisopropylcarboxamide)-4-bromo-estr-1,3,5(10)-triene-3-phosphinic acid.

EXAMPLE 13

17β-(N,N-Diisopropylcarboxamide)-2,4-dibromo-estr-1,3,5(10)-triene-3-phosphinic Acid (i)

2,4-Dibromo-estr-1,3,5(10)-triene-3-ol-17β-(N,N-diisopropylcarboxamide)

The title compound is prepared according to Example 12(i) by reacting estr-1,3,5(10)-triene-3-ol-17β-(N,N-diisopropylcarboxamide) with 2.0 equivalents of bromine.

(ii)

17β-(N,N-Diisopropylcarboxamide)-2,4-dibromo-estr-1,3,5(10)-triene-3-phosphinic Acid The title compound is prepared according to Example 12 (ii and iii) by substituting 2,4-dibromo-estr-1,3,5(10)-triene-3-ol-17β-(N,N-diisopropylcarboxamide) for 2-bromo estr-1,3,5(10)-triene-3-ol-17β-(N,N-diisopropylcarboxamide).

EXAMPLE 14

17β-(N,N-Diisopropylcarboxamide)-2-fluoro-estr-1,3,5(10)-triene-3-phosphinic Acid and
17β-(N,N-Diisocrocylcarboxamide)-4-fluoro-estr-1.3.5(10)-triene-3-phosphinic Acid The title compounds are prepared according to Example 1 by substituting methyl 2-fluoro-estrone and methyl 4-fluoro-estrone (prepared according to the procedures described by Neeman, *J. Chem. Soc. Perkin I* 2297 (1972) and *J. Chem. Soc. Perkin I* 2300 (1972)) for methyl estrone.

EXAMPLE 15

17β-(N,N-Diisopropylcarboxamide)-1-bromo-estr-1,3,5(10)-triene-3-phosphinic Acid (i)

4-Nitro-estr-1,3,5(10)-triene-3-ol-17β-(N,N-diisopropylcarboxamide)

A solution of estr-1,3,5(10)-triene-3-ol-17β-(N,N-diisopropylcarboxamide) (141 mg, 0.368 mmol) in boiling acetic acid (7 mL) is slowly cooled to 75° C. and treated with a solution of concentrated nitric acid (24.8 μL) in water (1.4 mL) containing a catalytic amount of sodium nitrite. The reaction mixture is allowed to slowly cool to room temperature, then is diluted with water and extracted with ethyl acetate The extract is washed thoroughly with water, dried, concentrated and purified by chromatography (silica gel, dichloromethane containing 5 to 10% ether) affording 55.2 mg (35%, mp 143.5°–144.5° C.) of 2-nitro-estr-1,3,5(10)-triene-3-ol-17β-(N,N-diisopropylcarboxamide) and 32.2 mg (20%, mp 239°–241° C.) of 4-nitro-estr-1,3,5(10)-triene-3-ol-17β-(N,N-diisopropylcarboxamide).

(ii) 3-Methoxy-4-nitro-estr 1,3,5(10)-triene-17β-(N,N-diisopropylcarboxamide)

A mixture of 4-nitro-estr-1,3,5(10)-triene-3-ol-17β-(N,N-diisopropylcarboxamide) (0.407 mmol), dimethyl sulfate (76.9 ml, 0.814 mmol), powdered anhydrous potassium carbonate (112 mg, 0.814 mmol) and acetone (10 ml) is refluxed under an argon atmosphere for 1.25 hours. The cooled reaction mixture is diluted with water and extracted with dichloromethane. The dichloromethane extract is washed with water, dried and concentrated to yield the title compound.

(iii)

1-Bromo-estr-1,3,5(10)-triene-3-ol-17β-(N,N-diisopropylcarboxamide)

The title compound is prepared according to the method of Hylarides (*J. Org. Chem.* 49, 2744(1984)) by substituting 3-methoxy-4-nitro-estr-1,3,5(10)-triene-17β-(N,N-diisopropylcarboxamide) for 4-nitro-methyl estrone.

(iv)
17β-(N,N-Diisopropylcarboxamide)-1-bromo-estr-1,3,5(10)-triene-3-phosphinic Acid The title compound is prepared according to Example 1 (v and vi) by substituting 1-bromo estr-1,3,5(10)-triene-3-ol-17β-(N,N-diisopropylcarboxamide) in Example 1 (v) for estr-1,3,5(10)-triene-3-ol-17β-(N,N-diisopropylcarboxamide) and subsequently proceeding with step (vi) of Example 1.

EXAMPLE 16

An oral dosage form for administering Formula (I) compounds is produced by screening, mixing, and filling into hard gelatin capsules the ingredients in the proportions shown in Table II, below.

TABLE II

| Ingredients | Amounts |
| --- | --- |
| 17β-(N,N-Diisopropylcarboxamide)-estr-1,3,5(10)-triene-3-phosphinic Acid | 50 mg |
| magnesium stearate | 5 mg |
| lactose | 75 mg |

EXAMPLE 17

The sucrose, calcium sulfate dihydrate and Formula (I) compound shown in Table III below, are mixed and granulated in the proportions shown with a 10% gelatin solution. The wet granules are screened, dried, mixed with the starch, talc and stearic acid, screened and compressed into a tablet.

TABLE III

| Ingredients | Amounts |
| --- | --- |
| 17β-(N-tert-Butylcarboxamide)-estr-1,3,5(10)-triene-3-phosphinic Acid | 100 mg |
| calcium sulfate dihydrate | 150 mg |
| sucrose | 20 mg |
| starch | 10 mg |
| talc | 5 mg |
| stearic acid | 3 mg |

EXAMPLE 18

17β-(N,N-Diisopropylcarboxamide)-estr-1,3,5(10),16-tetraene-3-phosphinic acid hydrochloride, 75 mg, is dispersed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

(I)

in which:
the B, C, and D rings have optional double bonds where indicated by the broken lines, provided that the C ring does not have a double bond when the B ring has a $C_8$–$C_9$ double bond, and provided that the D ring does not have a $C_{16}$–$C_{17}$ double bond when R represents two substituents or a divalent substituent;

$X^1$, $X^2$, and $X^3$ are any accessible combination of H, Cl, F, Br, I, $CF_3$, or $C_{1-6}$alkyl, OH, $C_{1-6}$alkoxy, CN, $NO_2$, $N(R^1)_2$, CHO, or $CO_2R^1$;

$R^1$ each independently is H or $C_{1-8}$alkyl; and
R is (1) α-hydrogen, α-hydroxyl, or α-acetoxy and/or (a)

$$-W-\overset{O}{\underset{\|}{C}}-R^2$$

where W is a bond or $C_{1-12}$alkyl, and $R^2$ is
(i) hydrogen,
(ii) hydroxyl,
(iii) $C_{1-8}$alkyl,
(iv) hydroxy $C_{1-8}$ alkyl,
(v) $C_{1-18}$alkoxy,
(vi) $N(R^3)_2$, where each $R^3$ is independently selected from hydrogen, $C_{1-8}$alkyl, $C_{3-6}$cycloalkyl, phenyl; or both $R^3$ taken together with the nitrogen to which they are attached represent a 5–6 member saturated ring comprising up to one other heteroatom selected from oxygen and nitrogen, or
(vii) $OR^4$, where $R^4$ is alkali metal or benzyl, or (b) —Alk—$OR^5$, where Alk is $C_{1-12}$alkyl, and $R^5$ is
(i) phenyl $C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl or $C_{1-8}$alkyl substituted aminocarbonyl or
(vi) $C_{1-8}$alkyl, (2) =CH—W—CO—$R^2$ or =CH—W—$OR^5$, where W is a bond or $C_{1-12}$alkyl and $R^2$ and $R^5$ have the same meaning as above and $R^5$ also is $C_{1-20}$alkylcarbonyl;

(3)

where the dashed bond replaces the 17-α-hydrogen (4) α-hydrogen and β-NHCOR$^6$ where $R^6$ is $C_{1-12}$alkyl or β-N($R^3$)$_2$ where $R^3$ has the same meaning as above, (5) α-hydrogen and β-cyano, (6) α-hydrogen and β-tetrazolyl, or (7) keto;

or a pharmaceutically acceptable salt thereof.

2. A compound of claim 1 having the following formula:

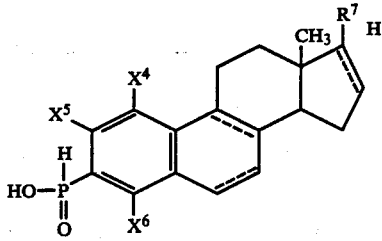

in which:
the B and D rings have optional double bonds where indicated by the broken lines, provided that the 17α-hydrogen is not present when the $C_{16}$–$C_{17}$ double bond is present;
$X^4$, $X^5$, and $X^6$ are H;
$R^7$ is
(a) $CH(CH_3)CH_2 OR^1$, or
(b) $CON(R^1)_2$ and
$R^1$ each independently is H or $C_{1-8}$alkyl;
or a pharmaceutically acceptable salt thereof.

3. A compound of claim 2 that is 17β-(N,N-diisopropylcarboxamide)-estr-1,3,5(10)-triene-3-phosphinic acid or a salt thereof.

4. A compound of claim 2 that is 17β-(N-tert-butylcarboxamide)-estr-1,3,5(10)-triene-3-phosphinic acid or a salt thereof.

5. A compound of claim 2 that is 17β-(N,N-diisopropylcarboxamide)-estr-1,3,5(10),16-tetraene-3-phosphinic acid or a salt thereof.

6. A compound of claim 2 that is 17β-(N-tert-butylcarboxamide)-estr-1,3,5(10),16-tetraene-3-phosphinic acid or a salt thereof.

7. A compound of claim 2 that is 17β-(N,N-diisopropylcarboxamide)-estr-1,3,5(10),6,8-pentaene-3-phosphinic acid or a salt thereof.

8. A compound of claim 2 that is 17β-(N,N-diisopropylcarboxamide)-estr-1,3,5(10),6-tetraene-3-phosphinic acid or a salt thereof.

9. A compound of claim 1 that is 17β-(N,N-diisopropylcarboxamide)-2-methyl-estr-1,3,5(10)-triene-3-phosphinic acid or a salt thereof.

10. A compound of claim 1 that is 17β-(N,N-diisopropylcarboxamide)-4-methyl-estr-1,3,5(10)-triene-3-phosphinic acid or a salt thereof.

11. A compound of claim 1 that is 17β-(N,N-diisopropylcarboxamide)-2-chloro-estr-1,3,5(10)-triene 3-phosphinic acid or a salt thereof.

12. A compound of claim 1 that is 17β-(N,N-diisopropylcarboxamide)-4-chloro-estr-1,3,5(10)-triene-3-phosphinic acid or a salt thereof.

13. A pharmaceutical composition comprising a suitable pharmaceutical carrier and a compound of claim 1.

14. A composition of claim 13 wherein the compound is 17β-(N,N-diisopropylcarboxamide)-estr-1,3,5(10)-triene-3-phosphinic acid or a salt thereof.

15. A composition of claim 13 wherein the compound is
17β-(N-tert-butylcarboxamide)-estr-1,3,5(10)-triene-3-phosphinic acid or a salt thereof,
17β-(N,N-diisopropylcarboxamide)-2-methyl-estr-1,3,5(10)-triene-3-phosphinic acid or a salt thereof,
17β-(N,N-diisopropylcarboxamide)-4-methyl-estr-1,3,5(10)-triene-3-phosphinic acid or a salt thereof,
17β-(N,N-diisopropylcarboxamide)-2-chloro-estr-1,3,5(10)-triene-3-phosphinic acid or a salt thereof,
17β-(N,N-diisopropylcarboxamide)-4-chloro-estr-1,3,5(10)-triene-3-phosphinic acid or a salt thereof,
17β-(N,N-diisopropylcarboxamide)-estr-1,3,5(10),16-tetraene-3-phosphinic acid or a salt thereof,
17β-(N-tert-butylcarboxamide)-estr-1,3,5(10),16-tetraene-3-phosphinic acid or a salt thereof,
17β-(N,N-diisopropylcarboxamide)-estr-1,3,5(10),6,8-pentaene-3-phosphinic acid or a salt thereof, or
17β-(N,N-diisopropylcarboxamide)-estr-1,3,5(10),6-tetraene-3-phosphinic acid or a salt thereof.

16. A method of inhibiting steroid 5-α-reductase activity in a subject that comprises administering internally to the subject an effective therefor amount of a compound of claim 1.

17. A method of claim 16 wherein the compound is 17β-(N,N-diisopropylcarboxamide)-estr-1,3,5(10)-triene-3-phosphinic acid or a salt thereof.

18. A method of claim 16 wherein the compound is
17β-(N-tert-butylcarboxamide)-estr-1,3,5(10)-triene-3-phosphinic acid or a salt thereof,
17β-(N,N-diisopropylcarboxamide)-2-methyl-estr-1,3,5(10) triene-3-phosphinic acid or a salt thereof,
17β-(N,N-diisopropylcarboxamide)-4-methyl-estr-1,3,5(10)-triene-3-phosphinic acid or a salt thereof,
17β-(N,N-diisopropylcarboxamide)-2-chloro-estr-1,3,5(10) triene-3-phosphinic acid or a salt thereof,
17β-(N,N-diisopropylcarboxamide)-4-chloro-estr-1,3,5(10)-triene-3-phosphinic acid or a salt thereof,
17β-(N,N-diisopropylcarboxamide)-estr-1,3,5(10),16-tetraene-3-phosphinic or a salt thereof,
17β-(N-tert-butylcarboxamide)-estr-1,3,5(10),16-tetraene-3-phosphinic acid or a salt thereof,
17β-(N,N-diisopropylcarboxamide)-estr-1,3,5(10),6,8-pentanene-3-phosphinic acid or a salt thereof, or
17β-(N,N-diisopropylcarboxamide)-estr-1,3,5(10),6-tetraene-3-phosphinic acid or a salt thereof.

19. A method of reducing or maintaining prostate size in a subject that comprises administering to a subject an effective therefor amount of a compound of claim 1.

20. A method of treating baldness in a subject that comprises administering to a subject an effective therefor amount of a compound of claim 1.

21. A method of treating acne in a subject that comprises administering to a subject an effective therefor amount of a compound of claim 1.

22. A method of treating hirsutism in a subject that comprises administering to a subject an effective therefor amount of a compound of claim 1.

* * * * *

UNITED STATES PATENT AND TRADEMARK OFFICE
CERTIFICATE OF CORRECTION

PATENT NO. : 4,937,237

DATED : June 26, 1990

INVENTOR(S) : Dennis A. Holt, Mark A. Levy and Brian W. Metcalf

It is certified that error appears in the above-identified patent and that said Letters Patent is hereby corrected as shown below:

Title page, in the title of the invention delete "60" and replace with --- $\alpha$ ---.

Column 1, line 2; in the title of the invention; delete "60" and replace with --- $\alpha$ ---.

Signed and Sealed this

First Day of October, 1991

Attest:

Attesting Officer

HARRY F. MANBECK, JR.

Commissioner of Patents and Trademarks